United States Patent [19]
Merianos et al.

[11] 3,960,538
[45] June 1, 1976

[54] AMINO DERIVATIVES OF TETRASUBSTITUTED BENZENE COMPOUNDS

[75] Inventors: John J. Merianos, Jersey City; Phillip Adams, Murray Hill, both of N.J.

[73] Assignee: Millmaster Onyx Corporation, New York, N.Y.

[22] Filed: Feb. 12, 1975

[21] Appl. No.: 549,170

Related U.S. Application Data

[60] Division of Ser. No. 360,448, May 15, 1974, Pat. No. 3,886,284, which is a continuation of Ser. No. 298,759, Oct. 18, 1972, abandoned, which is a continuation-in-part of Ser. No. 291,824, Sept. 25, 1972, Pat. No. 3,838,197, which is a continuation-in-part of Ser. No. 130,783, April 2, 1971, Pat. No. 3,821,407.

[52] U.S. Cl. .................................................. 71/67
[51] Int. Cl.² ........................................ A01N 9/20
[58] Field of Search ........................................ 71/67

[56] References Cited
UNITED STATES PATENTS 3,645,715  2/1972  Daum et al. ........................... 71/67
3,733,421  5/1973  Merianos et al. ................... 71/67 X
3,862,330  1/1975  Johnson et al. ...................... 71/67 X

*Primary Examiner*—Lewis Gotts
*Assistant Examiner*—Catherine L. Mills
*Attorney, Agent, or Firm*—Arthur A. Jacobs

[57] ABSTRACT

Antimicrobial 1,2,4,5-tetrasubstituted benzenes having the structure:

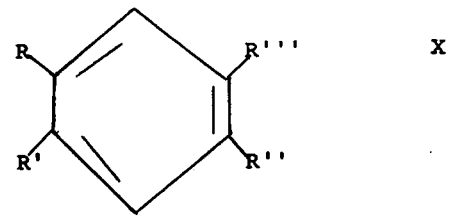

wherein R and R' may be methyl, or a halogen when R''' is —CH$_2$—; or R and R', taken together, may be methylene dioxy; R'' may be methyl or nitro; R''' may be absent or may be —CH$_2$— or —CH=; and X is the residue of a substituted amino or a polyamino radical.

5 Claims, No Drawings

AMINO DERIVATIVES OF TETRASUBSTITUTED BENZENE COMPOUNDS

This application is a division of co-pending application Ser. No. 360,448, filed May 15, 1974 now issued as U.S. Pat. No. 3,886,284, dated May 27, 1975; the latter being a continuation of co-pending application Ser. No. 298,759, filed Oct. 18, 1972, now abandoned; which is a continuation-in-part of application Ser. No. 291,824, filed Sept. 25, 1972 now issued as U.S. Pat. No. 3,838,197, dated Sept. 24, 1974; which is, in turn, a continuation-in-part of application Ser. No. 130,783, filed Apr. 2, 1971, now issued as U.S. Pat. No. 3,821,407, dated June 28, 1974.

This invention relates to novel and potent antimicrobial agents comprising amino derivatives of certain 1,2,4,5 tetra-substituted benzenes.

In accordance with the present invention, potent antimicrobial effects are obtained in the use of compounds having the general structure:

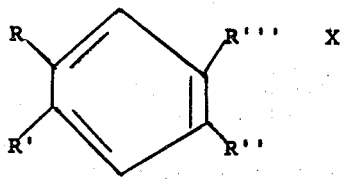

wherein R and R' may be methyl, or a halogen when R''' is —CH$_2$—; or R and R', taken together, may be methylene dioxy; R'' may be methyl or nitro; R''' may be absent or may be —CH$_2$— or —CH=; and X is the residue of a lower alkyl, mono- or polyamino, or alkanolamino radical.

The configuration of these tetrasubstituted benzenes is mainly, but not necessarily exclusively, 1,2,4,5. For example, the chloromethylation of pseudocumene to trimethylbenzyl chloride by methods known to the art produces about 80 to 85% of the 2,4,5-trimethylbenzyl chloride isomer; about 10–15% of the 2,3,5, isomer; about 10–15% of the 2,3,5 isomer; and small amounts of the 2,3,6 isomer. The chloromethylation of 1,2,4-trichlorobenzene yields a similar distribution.

Halogenation of pseudocumene also results in comparable isomeric distribution; of which, for example, the 5-halo trimethylbenzene is a solid, which is easily separated from its liquid isomers.

The antimicrobial amino derivatives of the present invention will be referred to hereinafter as the principal 1,2,4,5-components, with the understanding that minor amounts of the isomeric compounds may be present.

Among the intermediate agents with which the amino compounds described hereinafter are reacted to produce the products of the invention are trimethylbenzyl halides, trihalobenzyl halides, trimethylhalobenzenes, trimethyl benzaldehydes, and nitro-piperonal; the halogen in each case being selected from the group consisting of chlorine, bromine and iodine.

The amino compounds which are employed in condensation reactions to yield the products of the invention are organic amines, polyamines, or alkanolamines having at least one primary amino group, such, for example, as ethanolamine, ethylene diamine, propylene diamine, hydroxyethyl ethylene diamine, dimethylaminopropylamine, and the like.

The antimicrobial properties of these products or of their salts make them effective preservatives, sanitizing and disinfecting agents which are effective against bacteria, fungi and algae. They may be applied to the preservation of cosmetics and to the preservation of water-based paints, both in the emulsion and in the applied and dried film. They may also be used in the preservation of metal working fluids such as cutting and grinding oils, to prevent putrefaction. They are, additionally, effective for the treatment of process and cooling water in such fields as paper making and the like, and in heat exchangers, air conditioners, humidifiers and dehumidifiers and the like. They are useful for the sanitization of surfaces and, in fact, whereever an antibacterial agent may be required.

The following examples are intended to illustrate but not to limit the invention, except as claimed:

EXAMPLE 1

Pseudocumene was chloromethylated by the procedure described by R. D. Lake and B. B. Corson, in the Journal of Organic Chemistry, Volume 24, pp. 1823–24. The washed crude was distilled to separate the unreacted residue of hydrocarbon and the small residue of bis-chloromethylated material. The 2,4,5-trimethylbenzyl chloride was obtained in about 80% yield.

EXAMPLE 2

An agitated, round-bottomed flask fitted with a dropping funnel and a reflux condenser was charged with 150 grams or 2.5 mols of ethylene diamine, and the funnel was charged with 84 grams or 0.5 mol of the distilled chloromethyl trimethylbenzene of Example 1; this was added slowly, during about one half hour, to the amine at a temperature of about 120°C, or about the reflux temperature at atmospheric pressure. The cooled mass was checked for ionic chlorine content, which was found to be of the theoretical amount.

100 ml. of 30% caustic soda solution was added with agitation, to liberate the product from its hydrochloride salt. 500 ml. of chloroform was added, and the contents of the flask were transferred to a separating funnel.

The chloroform layer was tapped off, and transferred to a distilling flask wherein the chloroform was stripped off and recovered.

Distillation was continued, and the product, trimethylbenzylaminoethylamine, was recovered in 95% of the theoretical amount, distilling at 122°–125°C at 0.1 mm. pressure. It had an equivalent weight by titration, of 98.7, the theoretical being 96. The still bottoms represented about 5% of the amount of active product.

The hydrochloride salt was prepared, and found to have a melting point of 172°–174°C.

For commercial purposes, it is not necessary to distill the product, but merely to strip off the chloroform.

EXAMPLE 3

In the same manner as in Example 2, the reaction was carried out with, respectively, propylene diamine, 1,3-diaminopropane, dimethylaminopropylamine, hydroxyethyl ethylene diamine, diethylene triamine and ethanolamine, instead of ethylene diamine.

For example, with dimethylaminopropylamine the reflux temperature was 130°–140°C, with diethylene triamine 130°–150°C, etc.

In each case, the temperature range of about 120°–150°C is adequate for a reaction time of about one half hour.

In the case of the high-boiling amines, such as ethanolamine, hydroxyethyl ethylene diamine and the like, it is not necessary to strip off the excess by distillation under high vacuum. Instead, after the addition of caustic and water, the aqueous layer containing the excess amine can be separated from the oily layer, and, thereafter, the water can be largely stripped off from the amine to be recovered by distillation.

EXAMPLE 4

5-chloropseudocumene was prepared by chlorinating pseudocumene in chloroform, as described in Smith and Moyle's "The Jacobsen Reaction, IV", in the Journal of the American Chemical Society, Volume 58, page 8 (1936), whereby 5-chloropseudocumene was separated from 3-chloropseudocumene by crystallization, the latter being liquid.

5-bromopseudocumene was prepared similarly, brominating in chloroform and separating the crystalline 5-bromopseudocumene from the 3-isomer.

EXAMPLE 5

An agitated, round-bottomed flask fitted with a reflux condenser was charged with 20 grams or 0.1 mol of the 5-bromopseudocumene of Example 4 and 30 grams or 0.5 mol of ethylenediamine, plus 0.5 grams of cuprous chloride. This was heated under reflux and agitation at about 120°C and atmospheric pressure for 24 hours. When bromide in titration indicated substantially complete reaction, the excess amine was stripped off, and the cooled residue was treated with 30% aqueous caustic soda. The product, trimethylanilinoethylamine was extracted with chloroform and washed with salt solution. The extract was filtered and stripped of chloroform, and the product was recovered as a solid melting at 221°–225°C. The yield was 85–90% of the theoretical.

Similarly, ethanolamine substituted for ethylene diamine and reacted at 170°–175°C for 72 hours yielded trimethylanilinoethanol; and the amines of Example 3 in general may also be reacted.

EXAMPLE 6

1,2,4-trichlorobenzene was chloromethylated by methods known to the art; for example, by treatment with paraformaldehyde and HCl gas in 100% sulfuric acid; or with paraformaldehyde and chlorosulfonic acid in concentrated sulfuric acid. The separated and washed product was distilled in vacuo to separate from unreacted trichlorobenzene, to recover the 2,4,5-trichlorobenzylchloride in good yield.

EXAMPLE 7

23 Grams or 0.1 mol of 2,4,5-trichlorobenzyl chloride and 30 grams or 0.5 mol of ethylene diamine were mixed and heated on a steam bath for 4 to 6 hours until titration of chloride ion indicated essential completion of the reaction. The excess of ethylene diamine was stripped off and the residue was treated with 30% caustic soda and extracted with chloroform.

After distilling off the chloroform, the 2,4,5-trichlorobenzylaminoethylamine was distilled.

In a similar manner, the 2,4,5-trichlorobenzyl chloride was reacted with the amines of Example 3, to yield the corresponding trichlorobenzylamino derivatives.

EXAMPLE 8

Schiff bases were prepared by reacting the amines of Examples 1 and 3 with aromatic aldehydes.

The Sommelet reaction (described by Shacklett and Smith, among others, in the Journal of the American Chemical Society, Volume 75, pages 2654–57) was used reacting the trimethyl benzyl chloride of Example 1 with a 10% excess of hexamethylene tetramine and with formalin, in aqueous ethanol. Yields of about 60% of trimethylbenzaldehyde were obtained, in accordance with Shacklett's experience.

Thirty grams or 0.2 mol of the trimethyl-benzaldehyde and 23 grams or 0.225 mol of dimethylaminopropylamine in 100 ml. of benzene were heated at the reflux temperature, about 80°C, in an agitated flask fitted with a Dean and Stark moisture trap and refux condenser for about 2 hours. The theoretical amount of water distilled out.

The benzene and the excess of amine was stripped off, leaving 44 grams or 95% of the theoretical of 3-(2,4,5 trimethylbenzylidene)-1-dimethylaminopropylamine as a liquid.

EXAMPLE 9

In the same apparatus, 15 grams or 0.1 mol of 2,4,5-trimethylbenzaldehyde and 3 grams or 0.05 mol of ethylene diamine were reacted in benzene, distilling out 0.1 mol of water. The product, bis (2,4,5-benzilidene)-ethylene diamine was recovered as leafy white crystals melting at 110°–115°C.

EXAMPLE 10

Other substituted benzaldehydes were similarly reacted as in Examples 8 and 9; for example, 6-nitro piperonal (otherwise, 2-nitro-4, 5-methylenedioxybenzaldehyde) yielded, with ethylene diamine, (2-nitro-4, 5-methylenedioxybenzylidene)-ethylene diamine.

EXAMPLE 11

In the same manner, 6-nitropiperonal yielded 3-(2-nitro-4,5-methylenedioxybenzylidene) 1-dimethylaminopropylamine.

EXAMPLE 12

In the same manner as in Example 9, the nitro substituted piperonal was reacted with one half a molar equivalent of ethylene diamine to yield the corresponding bis-(-2-nitro)-4,5-benzylidene) diamine.

EXAMPLE 13

The Schiff bases of the preceding examples may be reduced, if it is so desired, to the corresponding-benzylamino derivatives; for example, by treatment with sodium borohydride in methanol, or by hydrogenation in the presence of Raney nickel.

EXAMPLE 14

The above compounds were tested for antimicrobial activity, using the "Standard Tube Dilution Test", which is common knowledge to those skilled in the art. This test utilizes a suitable nutrient broth which is treated to provide various concentrations of the antimicrobial candidates of this invention.

To the sterile broth contained in test tubes at 9 ml. volume was added 1.0 ml. of a dilution of test antimicrobial solution, at levels of 1,000, 500, 250, 100, 50, 10 and 5 parts per million respectively. Following this, each tube was inoculated with 0.1 ml. of a broth suspension of a 24 hour culture of the test bacteria or fungi, to give a final bacterial count of 1 to 10 million organisms per ml; or a fungi count of from 10,000 to 50,000 spores per ml; or 30,000 cells per ml. for algae.

The tubes so inoculated were incubated for 48 and 96 hours at 37°C for bacteria; or 14 days at 28°C for fungi, and 7 days for algae. Following the aforementioned incubation periods, the tubes were examined for the presence or absence of microscopic growth. The lowest concentration of test material not permitting microscopic growth is designated as the Minimum Inhibitory Level. The test organisms employed were:

Escherichia colo = E.C.
Pseudomonas aeruginosa = Ps. a.
Staphylococcus aureus = S.a.
Streptococcus faecalis = S.f.
Aspergillus niger = A.n.
Penicilium expansum = P. e.
Chlorella pyranoidosa = C.P.

In the following Table, for the sake of brevity, the derivatives of the given amine will be given as:

Trimethylbenzyl = TMB
Trimethylphenyl = TMP
Ethylene diamine = ED
Diethylene triamine = DT
Hydroxyethyl ethylene diamine = HEED
Dimethylaminopropylamine = DMAPA Table 1

|  | Parts per million of product inhibiting: | | | | | | |
|  | Gram Negative | | Gram Positive | | Fungus | | Algae |
| --- | --- | --- | --- | --- | --- | --- | --- |
| Product | E.c | Ps.a. | S.a. | S.f. | A.n. | P.e. | C.p. |
| TMB/ED | 50 | 100 | 100 | 50 | 50 | 50 | 10 |
| TMB/DT | 50 | 500 | 50 | 50 | 500 | 500 | 50 |
| TMB/HEED | 500 | 1000 | 50 | 50 | 500 | 500 | 50 |
| TMB/DMAPA | 500 | 1000 | 50 | 100 | 100 | 100 | 10 |
| TMB/DMAPA | 500 | 1000 | 50 | 100 | 100 | 100 | 10 |
| TMB/ED | 100 | 1000 | 100 | 500 | 500 | 1000 | 50 |
| Bis TMB/ED | 100 | 1000 | 100 | 100 | 100 | 500 | 50 |
| Bis TMB/DMAPA | 100 | 500 | 10 | 10 | 100 | 500 | 10 |
| TCB/DT | 100 | 100 | 50 | 50 | >1000 | >1000 | — |
| TCB/HEED | 500 | <1000 | <1000 | <1000 | <1000 | <1000 | — |
| TCB/ED | 100 | 250 | 100 | 100 | — | — | — |

The invention claimed is:

1. A method of inhibiting algae which comprises applying to said algae an effective amount of a compound having the structure:

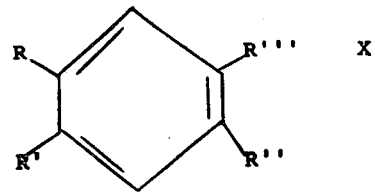

wherein R and R' are either methyl, or a halogen when R''' is —CH$_2$—; or R and R', taken together, are methylene dioxy; R'' is either methyl or nitro; R''' is either absent or is —CH$_2$— or —CH=; and X is the residue of a lower alkyl, mono- or polyamino, or alkanolamino radical.

2. The method of claim 1 wherein said compound is N-trimethylbenzyl-1,3-diaminopropane.

3. The method of claim 1 wherein said compound is N-trimethylbenzyl - N',N'-dimethyl - 1,3-diaminopropane.

4. The method of claim 1 wherein said compound is N-trimethylbenzyl - N' - hydroxyethyl ethylenediamine.

5. The method of claim 1 wherein said compound is N-trimethylbenzyl ethanolamine.

* * * * *